United States Patent
Hashimoto et al.

(10) Patent No.: US 6,177,587 B1
(45) Date of Patent: Jan. 23, 2001

(54) PRODUCTION METHOD OF AMINOBENZENE COMPOUND

(75) Inventors: Hideo Hashimoto, Takarazuka; Tadashi Hanaoka, Toyonaka; Masayasu Kato, Ashiya, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/080,456

(22) Filed: May 19, 1998

(30) Foreign Application Priority Data

May 26, 1997 (JP) .................................... 9-134195

(51) Int. Cl.$^7$ ................................ C07C 211/52
(52) U.S. Cl. ............................................ 558/414
(58) Field of Search .............................. 558/414

(56) References Cited

FOREIGN PATENT DOCUMENTS

| 0 425 921 A1 | 5/1991 | (EP) . |
| 0 459 136 A1 | 12/1991 | (EP) . |
| 0 553 879 A2 | 8/1993 | (EP) . |

OTHER PUBLICATIONS

Ries et al., J. Med. Chem., (36), 1993, 25, 4040–4051.*
Kubo et al.., J. Med. Chem., (36), 1993, 12, 1770–1784.*
Kubo et al., J. Med. Chem., (36), 1993, 15, 2182–2195.*
Jerry March, Advanced Organic Chemistry (Third edition), pp. 620–621, 1985.*
Jendralla et al., Liebigs Ann. (1995), (7), 1253–7 (Abstract).*

* cited by examiner

Primary Examiner—Mukund J. Shah
Assistant Examiner—Bruck Kifle
(74) Attorney, Agent, or Firm—Wenderoth, Lind & Ponack, L.L.P.

(57) ABSTRACT

The present invention is to provide an industrially useful production method of an aminobenzene compound represented by the formula:

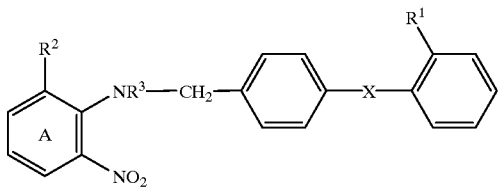

which is characterized by reacting a mixture of a mono-halogeno compound represented by the formula:

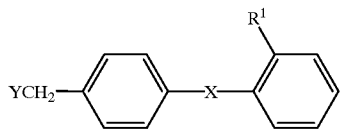

and di-halogeno compound represented by the formula:

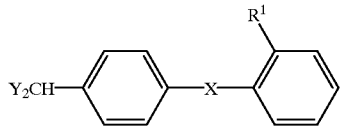

with a compound of the formula:

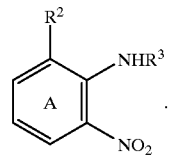

21 Claims, No Drawings

PRODUCTION METHOD OF AMINOBENZENE COMPOUND

FIELD OF THE INVENTION

The present invention relates to a industrially useful production method of an aminobenzene compound represented by the formula (IV) shown below which is of value as synthetic intermediates for the production of medicines.

BACKGROUND OF THE INVENTION

In Japanese Patent Laid-open Publication No. 364171/1992 (EP-A-459136), it is disclosed that benzimidazole derivatives including 1-(cyclohexyloxycarbonyloxy)ethyl 2-ethoxy-1-[[2'-(1H-tetrazol-5-yl)biphenyl-4-yl]methyl]benzimidazole-7-carboxylate, which have AII (angiotensin II) antagonizing activity and anti-hypertensive activity and which are of value as a therapeutic drug for circulatory diseases such as hypertension, heart diseases (e.g. heart hypertrophy, heart failure, myocardial infarction, etc.), cerebral stroke, nephritis, etc., and it is described that a compound represented by the formula (IV), which is important as a synthetic intermediate of the benzimidazole derivatives, is produced by the reaction of an aminobenzoate derivative represented by the formula (III) shown below with a mono-halogenoalkylbiphenyl compound (4-bromomethylbiphenyl (BMB), etc.) represented by the formula (II) shown below. Also, in Japanese Patent Laid-open Publication No. 192170/1994 (EP-A-553879), it is described that 4-bromomethylbiphenyl (BMB) is produced by brominating 4-methylbiphenyl (MPB) in the presence of an azobis compound.

According to a known production method of a compound or a salt thereof represented by the formula (II), it was believed that it was advantageous to isolate and purify a final product which was used as a material of a drug, since a perhalogenated compound represented by the formula (II') shown below was produced in the yield of about 10–20% at the time of halogenation of a compound or a salt thereof represented by the formula (I) shown below. Therefore, it was essential to increase purity (usually more than 99%) of a compound or a salt thereof represented by the formula (II) by crystallizing said compound after the halogenating reaction. In addition, in order to recover loss while crystallizing the first crystals and to raise purification effect, it was necessary to isolate the second crystals from mother liquor and dry after isolating and drying the first crystals. So far, the thus purified compound or a salt thereof represented by the formula (II) has been used as a material in the next steps. However, according to the above method, it was necessary to isolate the crystallized compound or a salt thereof represented by the formula (II) by a centrifuge, etc. and thereafter to dry by a drier, etc.

On the other hand, a compound or a salt thereof represented by the formula (II) is useful as an intermediate compound for producing a drug such as anti-hypertensive agent. However, since a compound of the formula (II) wherein $R^1$ is a cyano group, X is a direct bond and Y is a bromine atom is recognized to be strongly mutagenic and cause chromosomal aberrations, it was necessary to prevent the compound of the formula (II) from being exposed to workers producing the compound of the formula (II) and the environment.

According to a known method for producing a compound or a salt thereof represented by the formula (II), in order to prevent an isolated and purified compound or a salt thereof represented by the formula (II) from being exposed to the environment, a plant for producing said compound must be kept in isolation and, in order to prevent an isolated and purified compound or a salt thereof represented by the formula (II) from being exposed to the workers producing said compound, it was necessary to install an airtight centrifuge and drier, etc. However, it is very disadvantageous in view of industrial production to install such a special apparatus, etc. Moreover, according to a known method for producing a compound or a salt thereof represented by the formula (II), yield from a compound or a salt thereof represented by the formula (I) to a compound or a salt thereof represented by the formula (IV) is low and therefore not satisfactory as an industrial production method.

OBJECT OF THE INVENTION

The production method of the present invention is to provide an industrially advantageous method for producing a compound or a salt thereof represented by the formula (IV) by subjecting a compound or a salt thereof represented by the formula (I) to halogenation reaction and reacting the obtained reaction mixture with a compound or a salt thereof represented by the formula (III) without isolating or purifying a compound or a salt thereof represented by the formula (II).

SUMMARY OF THE INVENTION

The present inventors found that when a reaction mixture containing a compound or a salt thereof represented by the formula (II') and a compound or a salt thereof represented by the formula (II), which are obtained by halogenating reaction of a compound or a salt thereof represented by the formula (I), is subjected to reaction with a compound or a salt thereof represented by the formula (III), a compound or a salt thereof represented by the formula (II') does not react with a compound or a salt thereof represented by the formula (III) and that a compound or a salt thereof represented by the formula (IV) is selectively produced. Moreover, they found that when a compound or a salt thereof represented by the formula (IV) wherein $R^3$ is hydrogen atom, which is obtained by subjecting a compound or a salt thereof represented by the formula (IV) to hydrolysis reaction with a mineral acid such as hydrochloric acid, etc., is crystallized and a compound or a salt thereof represented by the formula (II') is removed in a mother liquor. Since a compound or a salt thereof represented by the formula (II') which does not react with a compound or a salt thereof represented by the formula (I) is easily removed, a compound or a salt thereof represented by the formula (IV) can be synthesized at a low price, in a good yield and advantageously in view of an industrial production without isolating and purifying a compound or a salt thereof represented by the formula (II), that is, without exposing a compound or a salt thereof represented by the formula (II) to the workers and environment. According to these findings, the present inventors have completed the present invention.

The present invention relates to (1) a method for producing an aminobenzene compound of the formula (IV):

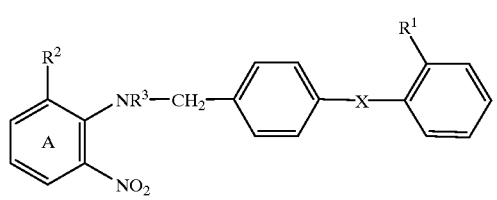
(IV)

wherein the ring A is a benzene ring which may have an optional substituent in addition to the group $R^2$, the nitro group and the group of the formula:

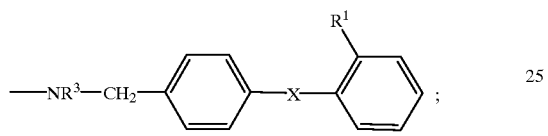

$R^1$ is a group capable of forming an anion or transformable thereinto;

$R^2$ is a group capable of forming an anion or transformable thereinto;

$R^3$ is an acyl group; and

X is a chemical bond or a spacer having a chain length of 1 to 2 atoms as the linear moiety between the adjoining phenylene group and phenyl group; or a salt thereof, which comprises reacting a mixture containing (i) a mono-halogeno compound of the formula (II):

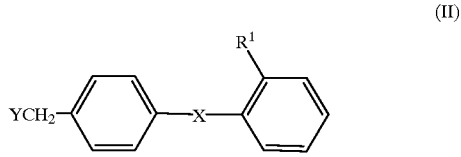
(II)

wherein Y is a halogen atom and the other symbols are as defined above, or a salt thereof and (ii) a di-halogeno compound of the formula (II'):

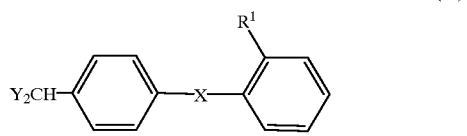
(II')

wherein each symbol is as defined above, or a salt thereof with a compound of the formula (III):

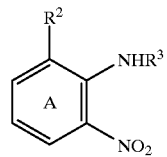
(III)

wherein the ring A is a benzene ring which may have an optional substituent in addition to the group $R^2$, the nitro group and the group of the formula: —$NHR^3$ and the other symbols are as defined above, or a salt thereof;

(2) a method of the above (1), wherein said reaction is carried out in acetonitrile;

(3) a method according (1), wherein the mixture is a reaction mixture which is obtained by subjecting a compound of the formula (I):

(I)

wherein $R^1$ is a group capable of forming an anion or transformable thereinto; and X is a chemical bond or a spacer having a chain length of 1 to 2 atoms as the linear moiety between the adjoining phenylene group and phenyl group; or a salt thereof to halogenation;

(4) a method of the above (1), wherein Y is a bromine atom;

(5) a method of the above (1), wherein $R^1$ is (1) a carboxyl group, (2) a tetrazolyl group, (3) a trifluoromethanesulfonamido group, (4) a phosphono group, (5) a sulfo group, (6) a 5–7 membered monocyclic heterocyclic group which contains one or more of N, S and O and which may be substituted;

(6) a method of the above (5), wherein the heterocyclic group is a group of the formula:

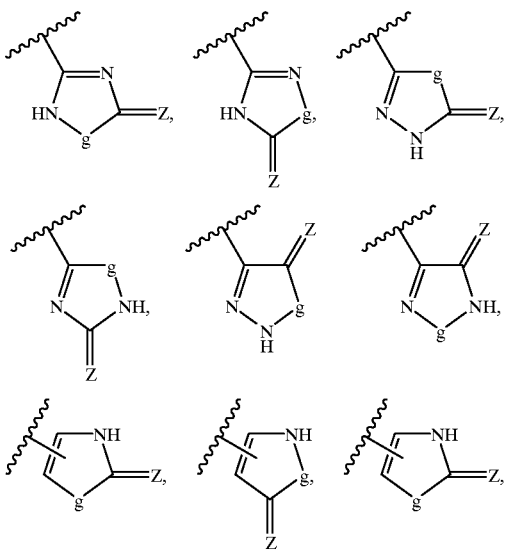

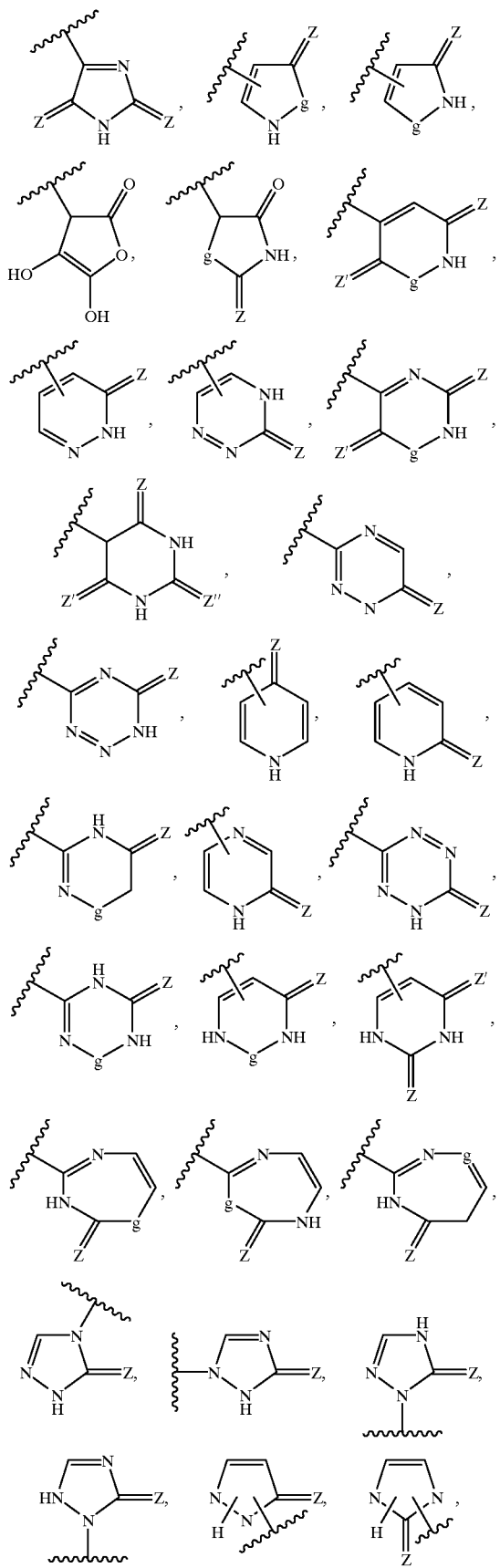

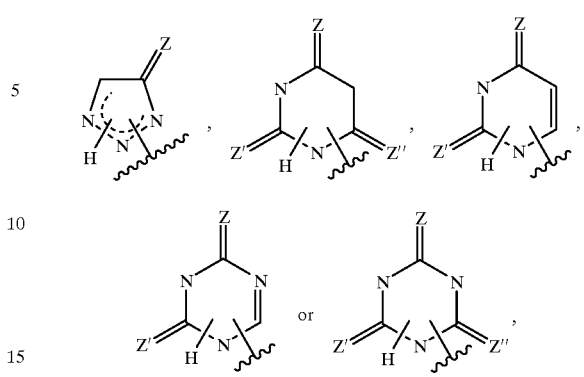

wherein g is —CH₂—, —NH—, —O— or —S(O)m—; >=Z, >=Z' and >=Z" are respectively a carbonyl group, a thiocarbonyl group or an optionally oxidized sulfur atom; and m is an integer of 0, 1 or 2, which may be protected by an optionally substituted lower ($C_{1-4}$) alkyl group or an acyl group and which may be substituted with an optionally substituted lower ($C_{1-4}$) alkyl group, a halogen atom, a nitro group, cyano, a lower ($C_{1-4}$)alkoxy group or an amino group optionally substituted with 1–2 lower ($C_{1-4}$) alkyl groups;

(7) a method of the above (5), wherein the heterocyclic group is an oxadiazolone ring, an oxadiazolothione ring or a thiadiazolone ring, which may be protected by an optionally substituted lower ($C_{1-4}$) alkyl group or an acyl group;

(8) a method of the above (5), wherein the heterocyclic group is a tetrazolyl group or a group of the formula:

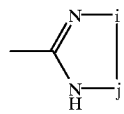

wherein the symbol i is —O— or —S—, the symbol j is >C=O, >C=S or >S(O)m, and m is an integer of 0, 1 or 2;

(9) a method of the above (1), wherein $R^1$ is (1) carboxyl, tetrazolyl or 2,5-dihydro-5-oxo-1,2,4-oxadiazol-3-yl each of which may be protected with an optionally substituted lower ($C_{1-4}$) alkyl or acyl group, or (2) cyano or N-hydroxycarbamimidoyl;

(10) a method of the above (1), wherein $R^1$ is cyano;

(11) a method of the above (1), wherein X is a direct bond, a lower ($C_{1-4}$) alkylene in which the number of atoms composing the straight chain is 1 or 2, —CO—, —O—, —S—, —NH—, —CO—NH—, —O—CH₂—, —S—CH₂— or —CH=CH—;

(12) a method of the above (1), wherein X is a direct bond;

(13) a method of the above (1), wherein the ring A has no substituent in addition to the group $R^2$, the nitro group and the group of the formula: —NHR³ unsubstituted or substituted

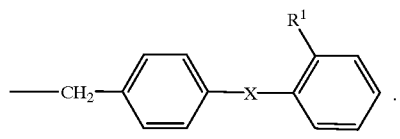

with a group of the formula:
(14) a method of the above (1), wherein $R^2$ is (1) an optionally esterified or amidated carboxyl group, (2) tetrazolyl group, (3) trifluoromethanesulfonamido group, (4) phosphono group or (5) sulfo group, which may be protected by an optionally substituted lower alkyl group or an acyl group;
(15) a method of the above (1), wherein $R^2$ is a group of the formula: —CO—D wherein D is an optionally substituted alkoxy group;
(16) a method of the above (1), wherein $R^2$ is a group of the formula: —CO—D wherein D is (1) hydroxy group or (2) a lower ($C_{1-4}$) alkoxy whose alkyl moiety may be substituted with hydroxy, amino, halogen, lower ($C_{2-6}$) alkanoyloxy, lower ($C_{3-8}$) cycloalkanoyloxy, lower ($C_{1-6}$)alkoxycarbonyloxy, lower ($C_{3-8}$) cycloalkoxycarbonyloxy, lower ($C_{1-4}$) alkoxy or lower ($C_{3-8}$) cycloalkoxy;
(17) a method of the above (1), wherein $R^2$ is a methoxycarbonyl group;
(18) a method of the above (1), wherein $R^3$ is a group of the formula: —$COR^8$ or —$COOR^8$ wherein $R^8$ is an optionally substituted hydrocarbon residue;
(19) a method of the above (18), wherein $R^8$ is a lower ($C_{1-5}$) alkyl or a lower ($C_{2-5}$) alkenyl group optionally substituted with hydroxy group, amino group, halogen or a lower ($C_{1-4}$) alkoxy group;
(20) a method of the above (1), wherein $R^3$ is t-butoxycarbonyl;
(21) a method of the above (1), wherein said reaction is carried out in the presence of potassium carbonate in acetonitrile;
(22) a method of the above (1), wherein said reaction is carried out between (1) a mixture containing 2-(4-bromomethylphenyl)benzonitrile and 2-(4,4-dibromomethylphenyl)benzonitrile and (2) methyl 2-tert-butoxycarbonyl-amino-3-nitrobenzoate to give methyl 2-[N-t-butoxycarbonyl-N-[(2'-cyanobiphenyl-4-yl)methyl]amino]-3-nitrobenzoate; etc.

In the above formulas, Y represents a halogen atom such as F, Cl, Br, I, etc. Among others, a bromine atom is preferable.

Examples of a group capable of forming an anion (a group having a hydrogen atom capable of leaving as a proton) represented by $R^1$ in the above formulas include, for example, (1) a carboxyl group, (2) a tetrazolyl group, (3) a trifluoromethanesulfonamido group (—$NHSO_2CF_3$), (4) a phosphono group, (5) a sulfo group, (6) a 5–7 membered (preferably 5–6 membered) monocyclic heterocyclic group which contains one or more of N, S and O and which may be substituted, etc.

Examples of the above a 5–7 membered (preferably 5–6 membered) monocyclic heterocyclic group which contains one or more of N, S and O include, e.g.,

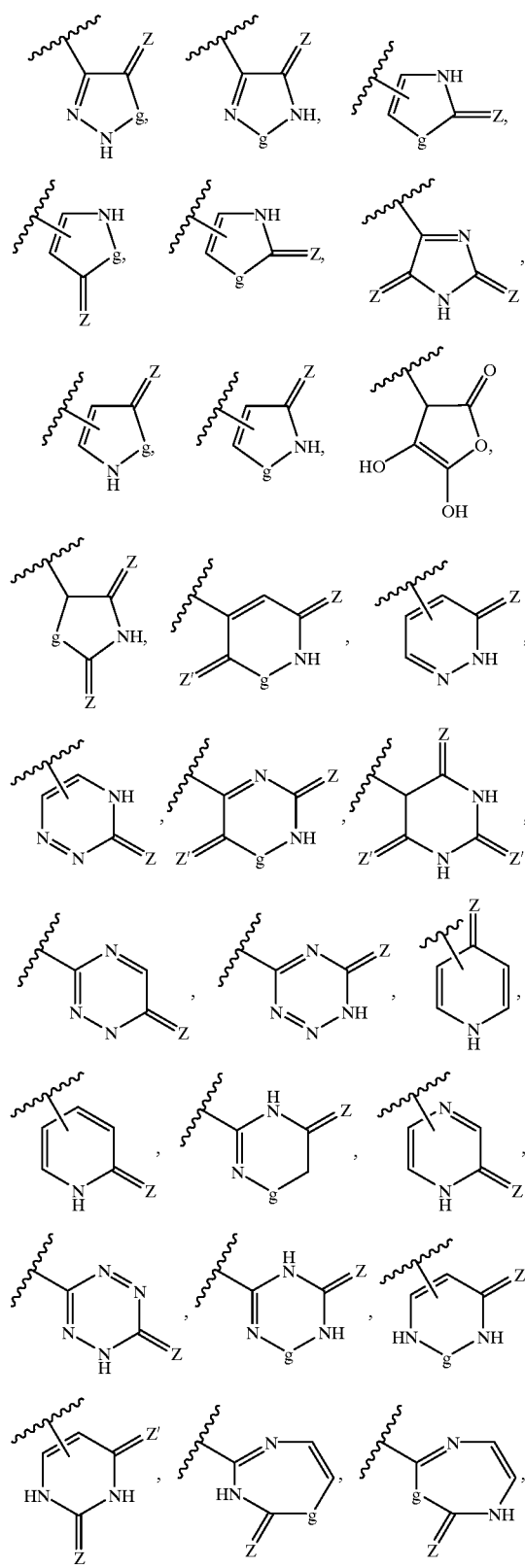

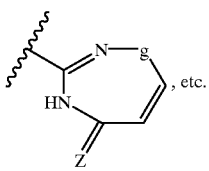, etc.

The chemical bond between the heterocyclic group represented by $R^1$ and the phenyl group to which said heterocyclic group binds may be a carbon-carbon bond as shown above and a nitrogen-carbon bond via one of the several nitrogen atoms when the symbol g is —NH—, etc. in the above formulas. For example, when $R^1$ represents

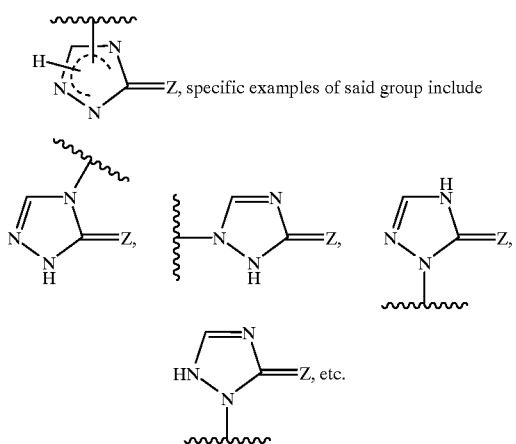

Other examples binding through the nitrogen atom include

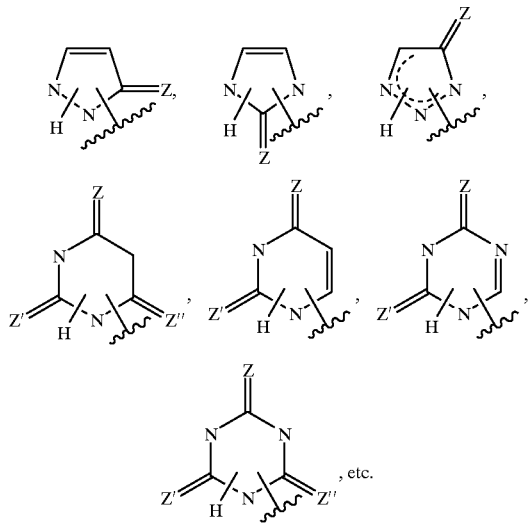

In the above groups g is —$CH_2$—, —NH—, —O— or —S(O)m—; and >=Z, >=Z' and >=Z" are respectively a carbonyl group (>C=O), a thiocarbonyl group (>C=S) or an optionally oxidized sulfur atom (e.g. >S, >S(O), >S(O)$_2$, etc.), preferably a carbonyl or thiocarbonyl group, more preferably a carbonyl group; and m is an integer of 0, 1 or 2.

Preferable examples of the heterocyclic group represented by $R^1$ are, for example, an oxadiazolone ring, an oxadiazolothione ring or a thiadiazolone ring, etc. which has —NH— group, —OH group etc. as proton donor and a carbonyl group, a thiocarbonyl group, a sulfinyl group, etc. as proton aceptor, simultaneously.

While the heterocyclic group represented by $R^1$ may form a condensed ring by connecting the substituents on the group, the heterocyclic group represented by $R^1$ is preferably a 5- to 6-membered ring, more preferably 5-membered ring.

Especially, as the heterocyclic group represented by $R^1$, a group of the formula:

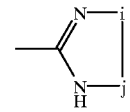

wherein the symbol i is —O— or —S—, the symbol j is >C=O, >C=S or >S(O)m, and m has the same meaning as defined above is preferable; more preferably 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl; in particular 2,5-dihydro-5-oxo-1,2,4-oxadiazol-3-yl.

In addition, the above-mentioned heterocyclic group ($R^1$) has the following tautomeric isomers. For example, in the group of the formula:

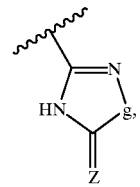

when Z=O, and g=O

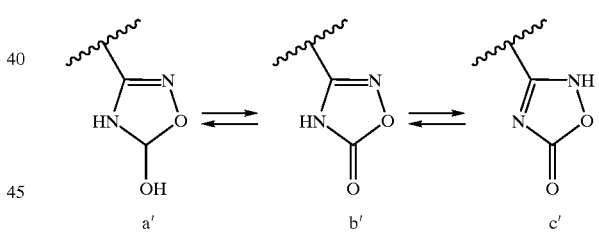

the above-described three tautomeric isomers a', b' and c' exist.

The heterocyclic group represented by the formula:

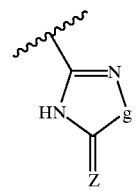

includes all of the above-mentioned a', b' and c'.

A group capable of forming an anion as the group $R^1$ may be protected by an optionally substituted lower ($C_{1-4}$) alkyl group, acyl group (e.g. a lower ($C_{2-5}$) alkanoyl, benzoyl, etc.), etc. at any possible position.

Examples of an optionally substituted lower ($C_{1-4}$) alkyl group include (1) a lower ($C_{1-4}$) alkyl group optionally substituted with 1–3 phenyl groups optionally having a halogen atom, a nitro group, a lower ($C_{1-4}$) alkyl, a lower ($C_{1-4}$) alkoxy, etc. (e.g. methyl, triphenylmethyl, p-methoxybenzyl, p-nitrobenzyl, etc.), (2) a lower ($C_{1-4}$) alkoxy-lower ($C_{1-4}$) alkyl group (e.g. methoxymethyl, ethoxymethyl, etc.), (3) a group of the formula: —CH($R^4$)—OCOR$^5$ wherein $R^4$ is (a) a hydrogen atom, (b) a straight or branched lower $C_{1-6}$ alkyl group (e.g. methyl, ethyl, n-propyl, isopropyl, n-butyl, isobutyl, t-butyl, n-pentyl, isopentyl, neopentyl, etc.), (c) a straight or branched lower ($C_{2-6}$) alkenyl group or (d) $C_{3-8}$ cycloalkyl group (e.g. cyclopentyl, cyclohexyl, cycloheptyl, etc.), and $R^5$ is (a) a straight or branched lower $C_{1-6}$ alkyl group (e.g. methyl, ethyl, n-propyl, isopropyl, n-butyl, isobutyl, sec-butyl, t-butyl, n-pentyl, isopentyl, neopentyl, etc.), (b) a straight or branched lower $C_{2-6}$ alkenyl group, (c) a lower $C_{1-3}$ alkyl group substituted with $C_{3-8}$ cycloalkyl group (e.g. cyclopentyl, cyclohexyl, cycloheptyl, etc.) or an optionally substituted aryl group (e.g. a phenyl or naphthyl group optionally having a halogen atom, a nitro group, a lower ($C_{1-4}$) alkyl, a lower ($C_{1-4}$) alkoxy, etc., etc.) such as benzyl, p-chlorobenzyl, phenethyl, cyclopentylmethyl, cyclohexylmethyl, etc.), (d) a lower ($C_{2-3}$) alkenyl group substituted with $C_{3-8}$ cycloalkyl or an optionally substituted aryl group (e.g. a phenyl or naphthyl group optionally having a halogen atom, a nitro group, a lower ($C_{1-4}$) alkyl, a lower ($C_{1-4}$) alkoxy, etc., etc.) such as cinnamyl, etc. having a alkenyl moiety such as vinyl, propenyl, allyl, isopropenyl, etc., etc., (e) an optionally substituted aryl group (e.g. a phenyl or naphthyl group optionally having a halogen atom, a nitro group, a lower ($C_{1-4}$)alkyl, a lower ($C_{1-4}$) alkoxy, etc., etc. such as phenyl, p-tolyl, naphthyl, etc.), (f) a straight or branched lower $C_{1-6}$ alkoxy group (e.g. methoxy, ethoxy, n -propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g. allyloxy, isobutenyloxy, etc.), (h) $C_{3-8}$ cycloalkyloxy group (e.g. cyclopentyloxy, cyclohexyloxy, cycloheptyloxy, etc.), (i) a lower $C_{1-3}$ alkoxy group substituted with $C_{3-8}$ cycloalkyl (e.g. cyclopentyl, cyclohexyl, cycloheptyl, etc.) or an optionally substituted aryl group (e.g. a phenyl or naphthyl group optionally having a halogen atom, a nitro group, a lower ($C_{1-4}$) alkyl, a lower ($C_{1-4}$) alkoxy, etc., etc.) such as benzyloxy, phenethyloxy, cyclopentylmethoxy, cyclohexylmethoxy, etc. having an alkoxy moiety such as methoxy, ethoxy, n-propoxy, isopropoxy, etc., (j) a lower $C_{2-3}$ alkenyloxy group substituted with $C_{3-8}$ cycloalkyl (e.g. cyclopentyl, cyclohexyl, cycloheptyl, etc.) or an optionally substituted aryl group (e.g. a phenyl or naphthyl group optionally having a halogen atom, a nitro group, a lower ($C_{1-4}$) alkyl, a lower ($C_{1-4}$) alkoxy, etc., etc.) such as cinnamyloxy, etc. having an alkenyloxy moiety such as vinyloxy, propenyloxy, allyloxy, isopropenyloxy, etc. or (k) an optionally substituted aryloxy group (e.g. a phenoxy or naphthoxy group optionally having a halogen atom, a nitro group, a lower ($C_{1-4}$) alkyl, a lower ($C_{1-4}$) alkoxy, etc., etc. such as phenoxy, p-nitrophenoxy, naphthoxy, etc.), etc.

A group capable of forming an anion represented by $R^1$ may have, in addition to the above-mentioned protective group such as an optionally substituted lower ($C_{1-4}$) alkyl group or acyl group (e.g. a lower ($C_{2-5}$) alkanoyl, benzoyl, etc.), etc., an optionally substituted lower ($C_{1-4}$) alkyl group (similar to the "optionally substituted lower ($C_{1-4}$) alkyl group" exemplified as the protective group for a group capable of forming an anion represented by the group $R^1$), a halogen atom, a nitro group, cyano, a lower ($C_{1-4}$)alkoxy group, an amino group optionally substituted with 1–2 lower ($C_{1-4}$) alkyl groups, etc. at any possible position.

In the above formula, examples of the group transformable into an anion, which is a group having a hydrogen atom capable of leaving as a proton, represented by $R^1$ include, any group (which is essential in so called pro-drug) transformable into an anion biologically or physiologically (e.g. through biological reactions such as oxidation, reduction, hydrolysis, etc. caused by enzymes in the body, etc.); and any group (which is essential in so called synthetic intermediate) transformable into an anion through chemical reactions such as cyano, N-hydroxycarbamimidoyl group (—C(=N—OH)—NH$_2$), and (1) carboxyl group, (2)tetrazolyl group, (3)trifluoro-methanesulfonamido group (—NHSO$_2$CF$_3$), (4) phosphono group, (5) sulfo group, (6) optionally substituted 5- to 7-membered (preferably 5- to 6-membered) monocyclic hetero-cyclic group containing one or more hetero atom selected from N, S and O, each of which is protected by an optionally substituted lower ($C_{1-4}$) alkyl group or an acyl group.

As $R^1$, (1) carboxyl, tetrazolyl or 2,5-dihydro-5-oxo-1,2,4-oxadiazol-3-yl (preferably tetrazolyl) each of which may be protected with an optionally substituted lower ($C_{1-4}$) alkyl (e.g. methyl, triphenylmethyl, methoxymethyl, ethoxymethyl, p-methoxybenzyl, p-nitrobenzyl, etc.) or acyl group (e.g. a lower ($C_{2-5}$) alkanoyl, benzoyl, etc.), or (2) cyano or N-hydroxycarbamimidoyl (preferably cyano) is preferable, and in particular cyano is preferable.

In the above formulas, X represents a covalent bond between the adjoining phenylene group and phenyl group or a spacer having a chain length of 1 or 2 atoms as the linear moiety between the adjoining phenylene group and phenyl group (preferably a covalent bond). The spacer having a chain length of 1 or 2 atoms may consist of a divalent chain in which the number of atoms composing the straight chain is 1 or 2 and may have a side chain. Specific examples of X include a lower ($C_{1-4}$) alkylene in which the number of atoms composing the straight chain is 1 or 2, —CO—, —O—, —S—, —NH—, —CO—NH—, —O—CH$_2$—, —S—CH$_2$—, —CH=CH—, etc.

In the above formulas, the ring A represents a benzene ring which may have an additional substituent other than the group $R^2$, the group of the formula: —NHR$^3$ unsubstituted or substituted with a group of the formula:

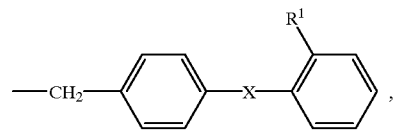

and the nitro group. Examples of said additional substituents include, for example, (1) halogen (e.g. F, Cl, Br, etc.), (2) cyano, (3) a nitro group, (4) an optionally substituted lower ($C_{1-4}$) alkyl, (5) a lower ($C_{1-4}$) alkoxy, (6) an optionally substituted amino group (e.g. amino , N-lower ($C_{1-4}$) alkylamino (e.g. methylamino, etc.), N,N-di-lower ($C_{1-4}$) alkylamino (e.g. dimethylamino, etc.), N-arylamino (e.g. phenylamino, etc.), alicyclic amino (e.g. morpholino, piperidino, piperazino, N-phenylpiperazino, etc.) etc.), (7) a group of the formula: —CO—D' wherein D' is hydroxy group or an optionally substituted lower ($C_{1-4}$) alkoxy whose alkyl moiety may be substituted with hydroxy group, a lower ($C_{1-4}$) alkoxy, a lower ($C_{2-6}$) alkanoyloxy (e.g. acetoxy, pivaloyloxy, etc.), a lower ($C_{1-6}$) alkoxycarbonyloxy (e.g. methoxy-carbonyloxy, ethoxy-carbonyloxy, etc.), a lower ($C_{3-6}$) cycloalkoxycarbonyloxy (e.g. cyclohexyloxycarbonyloxy, etc.), or (8) tetrazolyl, trifluoromethanesulfonamido group, phosphono group, sulfo group, etc. each of which may be protected by an optionally substituted lower ($C_{1-4}$) alkyl (similar to the "optionally substituted lower ($C_{1-4}$) alkyl group" exemplified as the protective group for a group capable of forming an anion as the group $R^1$) or acyl (e.g. a lower ($C_{2-5}$) alkanoyl, benzoyl, etc.).

One or two of these substituents may be concurrently present at any possible positions on the benzene ring. As the substituents which the ring A may have in addition to the group $R^2$, the group of the formula: —$NHR^3$ unsubstituted or substituted with a group of the formula:

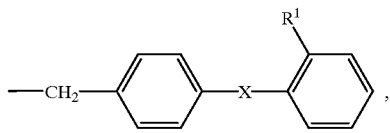

and the nitro group, an optionally substituted lower ($C_{1-4}$) alkyl (e.g. a lower ($C_{1-4}$) alkyl optionally substituted with hydroxy group, carboxyl group, halogen, etc., etc.), halogen, etc. are preferable and it is more preferable that the ring A in the formula (III) has no substituent in addition to the group $R^2$, the group of the formula: —$NHR^3$ unsubstituted and the nitro group; and the ring A in the formula (IV) has no substituent in addition to the group $R^2$, the group of the formula: —$NHR^3$ substituted with a group of the formula:

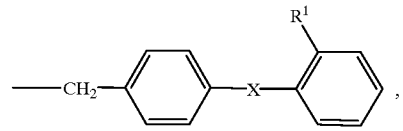

i.e., and the group of the formula:

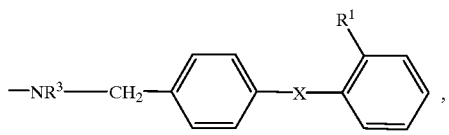

and the nitro group.

In the above formula, examples of the group capable of forming an anion (a group having a hydrogen atom capable of leaving as a proton) represented by $R^2$ include, for example, (1) optionally esterified or amidated carboxyl group, (2) tetrazolyl group, (3) trifluoromethanesulfonamido group (—$NHSO_2CF_3$), (4) phosphono group, (5) sulfo group, etc. These groups may be protected by an optionally substituted lower alkyl group (similar to the "optionally substituted lower ($C_{1-4}$) alkyl group" exemplified as a protective group for a group capable of forming an anion represented by $R^1$) or acyl group (e.g. a lower ($C_{2-5}$) alkanoyl, benzoyl, etc.). Any group capable of forming an anion or any group capable of forming an anion or transformable thereinto biologically or physiologically (e.g. through biological reactions such as oxidation, reduction, hydrolysis, etc. caused by enzymes in the body, etc.), or chemically is acceptable.

Examples of an optionally esterified or amidated carboxyl as the group $R^2$ include a group of the formula: —CO—D wherein D is (1) hydroxy group, (2) an optionally substituted amino (e.g. amino, N-lower ($C_{1-4}$) alkylamino, N,N-di-lower ($C_{1-4}$) alkylamino, etc.) or (3) an optionally substituted alkoxy. Specific Examples said optionally substituted alkoxy include (i) an optionally substituted lower ($C_{1-6}$) alkoxy group whose alkyl moiety may be substituted with a hydroxy group, an optionally substituted amino (e.g. amino, N-lower ($C_{1-4}$) alkylamino, N,N-di-lower ($C_{1-4}$) alkylamino, piperidino, morpholino, etc.), halogen, a lower ($C_{1-6}$) alkoxy, a lower ($C_{1-6}$) alkylthio, a lower ($C_{3-8}$) cycloalkoxy or an optionally substituted dioxolenyl (e.g. 5-methyl-2-oxo-1,3-dioxolen-4-yl, etc.), or (ii) a group of the formula: —O—CH($R^6$)—$OCOR^7$ wherein $R^6$ is (a) a hydrogen atom, (b) a straight or branched lower ($C_{1-6}$) alkyl group (e.g. methyl, ethyl, n-propyl, isopropyl, n-butyl, isobutyl, t-butyl, n-pentyl, isopentyl, neopentyl, etc.), (c) a straight or branched lower ($C_{2-6}$) alkenyl group or (d) $C_{3-8}$ cycloalkyl group (e.g. cyclopentyl, cyclohexyl, cycloheptyl, etc.), and $R^7$ is (a) a straight or branched lower ($C_{1-6}$) alkyl group (e.g. methyl, ethyl, n-propyl, isopropyl, n-butyl, isobutyl, sec-butyl, t-butyl, n-pentyl, isopentyl, neopentyl, etc.),(b) a straight or branched lower ($C_{2-6}$) alkenyl group, (c) a lower ($C_{1-3}$) alkyl group substituted with $C_{3-8}$ cycloalkyl group (e.g. cyclopentyl, cyclohexyl, cycloheptyl, etc.) or an optionally substituted aryl group (e.g. a phenyl or naphthyl group, etc. which may be substituted by a halogen atom, a nitro group, a lower ($C_{1-4}$) alkyl, a lower ($C_{1-4}$) alkoxy, etc.), such as benzyl, p-chlorobenzyl, phenethyl, cyclopentyl methyl, cyclohexylmethyl, etc., (d) a lower $C_{2-3}$ alkenyl group substituted with $C_{3-8}$ cycloalkyl or an optionally substituted aryl group (e.g. a phenyl or naphthyl group, etc. optionally having a halogen atom, a nitro group, a lower ($C_{1-4}$) alkyl, a lower ($C_{1-4}$) alkoxy, etc.) such as cinnamyl, etc. having alkenyl moiety such as vinyl, propenyl, allyl, isopropenyl, etc.), (e) an optionally substituted aryl group (e.g. a phenyl or naphthyl group, etc. optionally having a halogen atom, a nitro group, a lower ($C_{1-4}$) alkyl, a lower ($C_{1-4}$) alkoxy, etc. such as phenyl, p-tolyl, naphthyl, etc.), (f) a straight or branched lower $C_{1-6}$ alkoxy group (e.g. methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g. allyloxy, isobutenyloxy, etc.), (h) $C_{3-8}$ cycloalkyloxy group (e.g. cyclopentyloxy, cyclohexyloxy, cycloheptyloxy, etc.), (i) a lower $C_{1-3}$ alkoxy group substituted with $C_{3-8}$ cycloalkyl (e.g. cyclopentyl, cyclohexyl, cycloheptyl, etc.) or an optionally substituted aryl group (e.g. a phenyl or naphthyl group, etc. optionally having a halogen atom, a nitro group, a lower ($C_{1-4}$) alkyl, a lower ($C_{1-4}$) alkoxy, etc.) such as benzyloxy, phenethyloxy, cyclopentylmethoxy, cyclohexylmethoxy, etc. having alkoxy moiety such as methoxy, ethoxy, n-propoxy, isopropoxy, etc., (j) a lower $C_{2-3}$ alkenyloxy group substituted with $C_{3-8}$ cycloalkyl (e.g. cyclopentyl, cyclohexyl, cycloheptyl, etc.) or an optionally substituted aryl group (e.g. a phenyl or naphthyl group, etc. optionally having a halogen atom, a nitro group, a lower ($C_{1-4}$) alkyl, a lower ($C_{1-4}$) alkoxy, etc.) such as cinnamyloxy, etc. having vinyloxy, propenyloxy, allyloxy, isopropenyloxy, etc. or (k) an optionally substituted aryloxy group (e.g. a phenoxy or naphthoxy group, etc. optionally having a halogen atom, a nitro group, a lower ($C_{1-4}$) alkyl, a lower ($C_{1-4}$) alkoxy, etc.) such as phenoxy, p-nitrophenoxy, naphthoxy, etc.

As the group $R^2$, an optionally esterified carboxyl is preferable. Specific Examples of said optionally esterified carboxyl, include, for example, —COOH and a salt thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-ylmethoxycarbonyl, acetoxymethoxycarbonyl propionyloxymethoxycarbonyl, n-butyryloxymethoxy-carbonyl, isobutyryloxymethoxycarbonyl, 1-(ethoxycarbonyloxy) ethoxy-carbonyl, 1-(acetoxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl, etc. Any group capable of forming an anion or any group capable of forming an anion (e.g. COO—, its derivative, etc.) or transformable thereinto biologically or physiologically (e.g. through biological reactions such as oxidation, reduction, hydrolysis, etc. caused by enzymes in the body, etc.), or chemically is acceptable, and said group $R^2$ may be a carboxyl group or its pro-drug.

Among others, as the above group $R^2$, a group of the formula: —CO—D wherein D is (1) hydroxy group or (2) an optionally substituted lower ($C_{1-4}$) alkoxy whose alkyl moiety may be substituted with hydroxy, amino, halogen, lower ($C_{2-6}$) alkanoyloxy (e.g. acetooxy, pivaloyloxy etc.), lower ($C_{3-8}$) cycloalkanoyloxy, lower ($C_{1-6}$)alkoxycarbonyloxy (e.g. methoxycarbonyloxy, ethoxycarbonyloxy, etc.), lower ($C_{3-8}$) cycloalkoxycarbonyloxy (e.g. cyclohexyloxycarbonyloxy, etc.), lower ($C_{1-4}$) alkoxy or lower ($C_{3-8}$) cycloalkoxy is preferable, and in particular carboxyl esterified with lower ($C_{1-4}$) alkyl (preferably methyl or ethyl) is preferable.

In the above formulas, an acyl group represented by $R^3$ include, for example, a group of the formula: —$COR^8$ or —$COOR^8$ (preferably —$COOR^8$) wherein $R^8$ is an optionally substituted hydrocarbon residue, etc.

Examples of an optionally substituted hydrocarbon residue represented by $R^8$ include, for example, an alkyl group, an alkenyl group, an alkynyl group, a cycloalkyl group, an aryl group, an aralkyl group, etc. Among others, an alkyl group, an alkenyl group and a cycloalkyl group are preferable.

Examples of the alkyl group represented by $R^8$ include a straight or branched a lower $C_{1-8}$ alkyl group such as methyl, ethyl, propyl, isopropyl, butyl, isobutyl, sec-butyl, t-butyl, pentyl, i-pentyl, hexyl, heptyl, octyl, etc.

Examples of the alkenyl group represented by $R^8$ include a straight or branched a lower $C_{2-8}$ alkenyl group such as vinyl, propenyl, 2-butenyl, 3-butenyl, isobutenyl, 2-octenyl, etc.

Examples of the alkynyl group represented by $R^8$ include a straight or branched a lower $C_{2-8}$ alkynyl group such as ethynyl, 2-propynyl, 2-butynyl, 2-pentynyl, 2-octynyl, etc.

Examples of the cycloalkyl group represented by $R^8$ include a lower $C_{3-6}$ cycloalkyl such as cyclopropyl, cyclobutyl, cyclopentyl, cyclohexyl, etc.

Each of the above mentioned alkyl group, alkenyl group, alkynyl group or cycloalkyl group may be optionally substituted with a hydroxy group, an optionally substituted amino group (e.g. amino, N-lower ($C_{1-4}$) alkylamino, N,N-di-lower ($C_{1-4}$) alkylamino, etc.), halogen, a lower ($C_{1-4}$) alkoxy group, a lower ($C_{1-4}$) alkylthio group, etc.

Examples of the aralkyl group represented by $R^8$ include phenyl-lower ($C_{1-4}$) alkyl, etc. such as benzyl, phenethyl, etc. and examples of the alkyl group represented by $R^8$ include phenyl, etc.

Each of the above mentioned aralkyl group or aryl group may have, at any possible position of the benzene ring, for example, halogen (e.g. F, Cl, Br, etc.), a nitro group, an optionally substituted amino group(e.g. amino, N-lower ($C_{1-4}$) alkylamino, N,N-di-lower ($C_{1-4}$) alkylamino, etc.), a lower ($C_{1-4}$) alkoxy (e.g. methoxy, ethoxy, etc.), a lower ($C_{1-4}$) alkylthio (e.g. methylthio, ethylthio, etc.), a lower ($C_{1-4}$) alkyl (e.g. methyl, ethyl, etc.), etc.

Among others, as the group $R^8$, an optionally substituted alkyl or alkenyl group (e.g. a lower ($C_{1-5}$) alkyl or a lower ($C_{2-5}$) alkenyl group optionally substituted with hydroxy group, amino group, halogen or a lower ($C_{1-4}$) alkoxy group, etc.) is preferable and in particular a lower ($C_{1-5}$) alkyl (more preferably t-butyl) is preferable.

As the salt of a compound represented by the formulas (I), (II), (II'), (III) or (IV), any salts can be employed, unless they disturb the reaction of the present invention. Preferable examples of the salts include a salt with an inorganic base, a salt with an organic base, a salt with an inorganic acid, a salt with an organic acid, a salt with a basic or acidic amino acid, etc. Preferable examples of the salt with an inorganic base include an alkali metal salt such as sodium salt, potassium salt, etc.; an alkaline earth metal salt such as calcium salt, magnesium salt, etc.; aluminum salt; ammonium salt; etc. Preferable examples of the salt with an organic base include a salt with trimethylamine, triethylamine, pyridine, picoline, ethanolamine, diethanolamine, triethanolamine, dicyclohexylamine, N,N'-dibenzylethylenediamine, etc.

Preferable examples of the salt with an inorganic acid include hydrochloride, hydrobromide, nitrate, sulfate, phosphate, etc. Preferable examples of the salt with an organic acid include formate, acetate, trifluoroacetate, fumarate, oxalate, tartarate, maleate, citrate, succinate, malate, methanesulfonate, benzene sulfonate, p-toluenesulfonate, etc.

Preferable examples of the salt with a basic amino acid include a salt with arginine, lysine, ornithine, etc. Preferable examples of the salt with an acidic amino acid include a salt with aspartic acid, glutamic acid, etc.

When a compound or a salt thereof represented by the formula (I) is subjected to halogenation reaction, a method described in Japanese Patent Laid-open Publication No. 6-192170 or a method similar thereto can be employed. Usually, per mole of a compound or a salt thereof represented by the formula (I), about 1–2 moles of a halogenating agent such as N-bromosuccinimide (NBS), 1,3-dibromo-5,5-dimethylhydantoin, N-bromoacetamide, N-bromophthalimide, N-bromomaleimide, N-bromosulfonamide, etc. (preferably N-bromosuccinimide (NBS), 1,3-di-bromo-5,5-dimethylhydantoin, etc.) are used. Said halogenation reaction is preferably carried out in the presence of a radical starting agent such as heat, light, benzoyl-peroxides, azobis compounds, etc. Among others, azobis compounds are preferably employed.

Examples of the azobis compounds include 2,2'-azobis(2,4-dimethylvaleronitrile), 2,2'-azobis(2-methylbutyronitrile), azobisisovaleronitrile, 1,1'-azobis(cyclohexanecarbonitrile), 2,2'-azobis(4-methoxy-2,4-dimethylvaleronitrile), 2,2'-azobis(2-amidinopropane)hydrochloride, dimethyl-2,2'-azobisisobutyrate, etc. Among others, 2,2'-azobis(2,4-dimethylvaleronitrile), 2,2'-azobis-isobutyronitrile (AIBN) and 2,2'-azobis-(2,4-dimethylvaleronitrile) are preferable, and in particular 2,2'-azobis(2,4-dimethylvalero-nitrile) is preferable. The proportion of said azobis compound is about 0.1–3% based on the halogenating agent. The preferred proportion is about 2–3% for 2,2'-azobis-isobutyronitrile (AIBN) and about 0.1–0.3% for 2,2'-azobis(2,4-dimethylvaleronitrile).

Examples of the reaction solvent include halogenated hydrocarbons such as dichloromethane, chloroform, carbon tetrachloride, dichloroethane, etc., ethers such as tetrahydrofuran, dioxane, etc., esters such as ethyl acetate, etc., aromatic hydrocarbons such as benzene, toluene, xylene, etc., aprotic polar solvents such as dimethylformamide, dimethylsulfoxide, dimethylacetamide, etc., etc. Among others, halogenated hydrocarbons is preferable and in particular dichloromethane is preferable.

The solvents are preferably used in the amount of about 100–10000 ml per 1 mole of a compound or a salt thereof represented by the formula (I). A mixture containing a compound or a salt thereof represented by the formula (II) and a compound or a salt thereof represented by the formula (II') is produced by stirring the reaction solution at about 20–100° C., preferably 40–60° C., for about 1–10 hours, preferably for about 2–6 hours, in the above solvents and the concentrate containing a compound or a salt thereof represented by the formula (II) and a compound or a salt thereof represented by the formula (II') is obtained by adding water to the mixture and concentrating the organic layer. The obtained concentrate is preferably subjecting to alkylating reaction of a compound or a salt thereof represented by the formula (III), without isolating and purifying a compound or a salt thereof represented by the formula (II).

In the mixture containing a compound or a salt thereof represented by the formula (II) and a compound or a salt thereof represented by the formula (II'), it is preferable to use about 1/20 to about 1 mole of the compound or a salt thereof represented by the formula (II'), more preferably about 1/16 to 1/4 mole of the compound or a salt thereof represented by the formula (II'), relative to 1 mole of the compound or a salt thereof represented by the formula (II).

Said alkylating reaction of a compound or a salt thereof represented by the formula (III) with a mixture containing a compound or a salt thereof represented by the formula (II) and a compound or a salt thereof represented by the formula (II') is carried out by a method described in Japanese Patent Laid-open Publication No. 4-364171 or a similar method thereto. Usually, about 0.8–2 moles of a compound or a salt thereof represented by the formula (III), preferably 0.95–1.1 moles, are used per 1 mole of a compound or a salt thereof represented by the formula (II).

Said alkylating reaction is preferably carried out in the presence of base and examples of the base include metal hydrides such as sodium hydride, etc., metal alkoxides such as sodium t-butoxide, potassium t-butoxide, etc., carbonates such as potassium carbonate, potassium hydrogen carbonate, sodium carbonate, sodium hydrogen carbonate, etc. Among others, carbonates are preferable and in particular potassium carbonate is preferable. Said base is preferably used in the amount of about 1–5 moles per 1 mole of a compound or a salt thereof represented by the formula (II).

Examples of the reaction solvent include aprotic polar solvents such as dimethylformamide, dimethylsulfoxide, dimethylacetoamide, etc., ketones such as acetone, ethylmethylketone, etc., ethers such as tetrahydrofuran, dioxane, etc., esters such as ethyl acetate, etc., aromatic hydrocarbons such as benzene, toluene, xylene, etc., halogenated hydrocarbons such as dichloromethane, chloroform, carbon tetrachloride, dichloroethane, etc., acetonitrile, etc. Among others, acetonitrile is preferably used. The solvents are preferably used in the amount of about 100–10000 ml per 1 mole of a compound or a salt thereof represented by the formula (II). Only a compound or a salt thereof represented by the formula (IV) can be selectively produced by stirring the reaction solution at about 70–90° C. for about 3–10 hours in the above solvents, without producing a compound or a salt thereof represented by the formula (IV'):

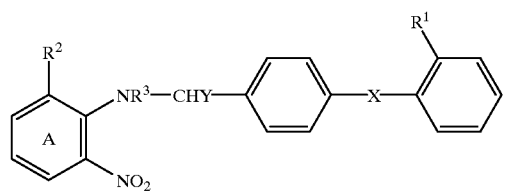

wherein each symbol is as defined above.

According to the above method, a compound or a salt thereof represented by the formula (IV) can be synthesized at a low price, in a good yield and advantageously in view of an industrial production without exposing a salt thereof represented by the formula (II) to the workers and environment.

After the reaction has been completed, the reaction solution is cooled and an inorganic salt is removed, and thereafter the obtained solution is concentrated and the obtained residue is dissolved in a solvent such as methanol, etc. To the solution is added a mineral acid such as hydrochloric acid, etc. and the solution is stirred for about 1–10 hours under reflux. By cooling the solution, a compound or a salt thereof represented by the formula (IV) wherein $R^3$ is hydrogen atom is precipitated and said compound can be used as a material compound in the next steps.

Effect of the Invention

As described above, according to the production method of the present invention, a compound or a salt thereof represented by the formula (IV) is easily produced in a completely airtight system and, therefore, it is not necessary to install a special apparatus, etc. in order to prevent a compound or a salt thereof represented by the formula (II) having strong mutagenicity from being exposed to the workers producing said compound and to the environment. Thus, the present invention provides an industrially advantageous method for producing a compound or a salt thereof represented by the formula (IV).

In addition, when a compound similar to a desired intermediate compound [e.g. a compound having a similar structure and a similar chemical property to a desired intermediate compound, such as a compound represented by the formula (II') compared with a compound represented by the formula (II)] is produced during a step for producing a drug, it is usual to remove said compound similar to a desired intermediate compound as early as possible during the steps for producing a drug, in order to cut down production costs (in other words, to prevent a material compound from being consumed by a reaction between a material compound and the compound similar to a desired intermediate compound) and to prevent impure substances (a compound similar to a final product, which is usually hard to be separated from the final product) from mixing with a final product. However, according to the production method of the present invention, a compound or a salt thereof represented by the formula (II') does not react with a compound or a salt thereof represented by the formula (III) [that is, there is no extra consumption of a compound or a salt thereof represented by the formula (III) and a compound or a salt thereof represented by the formula (IV') is not synthesized], even if the compound or a salt thereof represented by the formula (II') coexists with a compound or a salt thereof represented by the formula (II). Therefore, it is not necessary to separate a compound or a salt thereof represented by the formula (II) from a compound or a salt thereof represented by the formula (II'). Thus, it is possible to simplify the steps for producing a compound or a salt thereof represented by the formula (IV) and, moreover, to prevent a compound or a salt thereof represented by the formula (II) having strong mutagenicity from being exposed to the workers producing said compound and to the environment, and therefore, the production method of the present invention is an industrially advantageous method for producing a compound or a salt thereof represented by the formula (IV).

Furthermore, according to the production method of the present invention, it is industrially advantageous to produce a compound or a salt thereof represented by the formula (IV) since the compound or a salt thereof represented by the formula (IV) can be produced in good yield (which increases 10% or more, compared with a known production method).

EXAMPLES

The present invention is explained in further detail by the following Working Examples, Comparative Examples and Reference Examples but the present invention is not limited thereto.

Working Example 1

Production of methyl 2-[[(2'-cyanobiphenyl-4-yl) methylamino]-3-nitro-benzoate [MBN]

A mixture of 2-(4-methylphenyl)benzonitrile [MPB] 23 g, NBS 22 g and 2,2'-azobis(2,4-dimethylvaleronitrile) 47 mg was suspended in dichloromethane 44 ml and the mixture was stirred at 45–50° C. for about 5 hours. To the reaction mixture was added water 46 ml and the organic layer was separated. This operation was conducted three times. The organic layer was concentrated and acetonitrile 50 ml was added to the concentrate. The solution was again concentrated and acetonitrile 50 ml was added to the concentrate to give acetonitrile solution of 2-(4-bromomethylphenyl) benzonitrile [BMB] (116 g; Yield based on the theoretical amount of (2-(4-bromomethylphenyl)benzonitrile: 84%).

To the acetonitrile solution where BMB is mixing with 2-(4-methylphenyl)benzonitrile [MPB] which was not brominated and 2-(4,4-dibromomethylphenyl)benzonitrile which is a compound similar to BMB, was added a mixture of methyl 2-tert-butoxycarbonylamino-3-nitrobenzoate [BAN] 30.1 g, potassium carbonate 40.8 g and acetonitrile 160 ml and the solution was stirred at about 82° C. for about 5 hours to proceed the reaction. The solution was cooled to room temperature and precipitated crystals were filtered off. The filtrate was concentrated to give methyl 2-[N-t-butoxycarbonyl-N-[(2'-cyano-biphenyl-4-yl)methyl]amino]-3-nitrobenzoate [BBN]. The concentrate was dissolved in methanol 190 g. To the methanol solution was dropped concentrated hydrochloric acid 106 g and the solution was heated to refluxing temperature for 2 hours and thereafter stirred under reflux for 2 hours to proceed the reaction. The reaction solution was cooled and the precipitated crystals were filtered and dried to give methyl 2-[N-(2'-cyanobiphenyl-4-yl)methylamino]-3-nitrobenzoate [MBN] 35.1 g (yield based on 2-(4-methylphenyl) benzonitrile [MPB]: 76.1%).

Comparative Example 1

Production of methyl 2-[[(2'-cyanobiphenyl-4-yl) methylamino]-3-nitro-benzoate [MBN]

A mixture of 2-(4-methylphenyl)benzonitrile [MPB] (30 g), N-bromosuccinimide [NBS] (28.35 g), 2,2'-azobis(2,4-dimethylvaleronitrile) [ABN-V] (60 mg) and methylene chloride (75 g) was stirred at 45–50° C. for 3–4 hours under reflux. The reaction solution was cooled to 38–42° C. and washed with water (60 g) three times. The methylene chloride layer was discolored with activated charcoal (0.15 g) and was concentrated under reduced pressure. To the solution was added crystal seeds (0.01 g). The solution was cooled to not more than 5° C. and crystals were isolated and dried to obtain the first crystals of 4-(2-bromomethylphenyl) benzonitrile [BMB] (25.3 g, 60%). The second crystals were obtained from mother liquor (5.3 g, 13%).

To the obtained first and second crystals of BMB (30.6 g) were added a mixture of methyl 2-tert-butoxycarbonylamino-3-nitrobenzoate [BAN] 33.7 g, potassium carbonate 45.5 g and acetonitrile 280 g and the solution was stirred at about 82° C. for about 5 hours to proceed the reaction. The solution was cooled to room temperature and the precipitated crystals were filtered off. The filtrate was concentrated to give methyl 2-[N-t-butoxycarbonyl-N-[(2'-cyanobiphenyl-4-yl)methyl]amino]-3-nitrobenzoate [BBN].

The concentrate was dissolved in methanol 213 g. To the solution was dropped concentrated hydrochloric acid 119 g, and the solution was heated to refluxing temperature for 2 hours and further stirred for 2 hours under reflux to proceed the reaction. The reaction solution was cooled and the precipitated crystals were filtered and dried to give methyl 2-[N-(2'-cyanobiphenyl-4-yl)methylamino]-3-nitrobenzoate [MBN] 27.9 g (yield based on 2-(4-methylphenyl) benzonitrile [MPB]: 66%).

Reference Example 1

Production of methyl 2-carboxy-3-nitrobenzoate [MNA]

A mixture of 3-nitrophtalic acid [NPA] (660 kg), trimethyl orthoformate (400 kg), concentrated sulfuric acid (115 kg) and methanol (1180 kg) was stirred under reflux at 59–65° C. for about 15–20 hours. The reaction solution was cooled and concentrated under reduced pressure at not more than 40° C. The residue was cooled to not more than 30° C., to which was added water (900 L), and the solution was cooled to not more than 5° C. The precipitated crystals were centrifuged, washed with water and dried at 50° C. for about 50 hours to give methyl 2-carboxy-3-nitrobenzoate [MNA] (666.8 kg, 94.7%).

m.p. 166–168° C.

$^1$H-NMR(200 MHz,CDCl$_3$) δ: 4.03 (3H,s), 7.74(1H,t), 8.39(1H,dd), 8.42(1H,dd)

Reference Example 2

Production of methyl 2-t-butoxycarbonylamino-3-nitrobenzoate [BAN]

In dimethylformamide [DMF] (242 kg) was dissolved methyl 2-carboxy-3-nitrobenzoate [MNA] (164 kg) obtained in Reference Example 1. To the solution was dropped diphenylphosphorylazide [DPPA] (204 kg) at room temperature and then triethylamine (87 kg) at the temperature ranging 20–35° C. After the solution was stirred at 20–30° C. for about 3 hours, t-butylalcohol (930 kg) was added to the reaction solution. The solution was heated for 3–5 hours to 85–90° C. and then stirred for 1–2 hours under reflux (85–90° C.). The reaction solution was cooled, concentrated and dissolved in ethyl acetate(1400 L). The solution was washed with a mixture of 15% hydrochloric acid (160 L) and water (1890 L), water (660 L), 5% solution of sodium bicarbonate (1100 kg), and water (660 L), in this order and the organic layer was concentrated under reduced pressure. To the concentrate was added methanol (300 kg) and then were added crystal seeds (15 kg) and methanol (450 kg). The solution was heated to 50–60° C. to dissolve insoluble materials. The solution was cooled to 5° C. and precipitated crystals were separated. The crystals were washed with cooled methanol (100 L) and dried to give methyl 2-t-butoxycarbonylamino-3-nitrobenzoate [BAN] (187.0 kg, 86.7%). Mother liquor and the methanol solution used for washing the crystals was concentrated under reduced pressure and cooled. The precipitated crystals were centrifuged, washed with cooled methanol and dried to obtain the second crystals of BAN.

$^1$H-NMR (200 MHz, CDCl$_3$) δ: 1.50 (9H, s), 3.96 (3H, s), 7.23 (1H, t), 8.10 (1H, dd), 8.17 (1H, dd)

IR (KBr) cm$^{-1}$: 3360, 1730, 1705, 1580, 1520, 1490, 1440, 1365, 1355, 1310, 1270, 1240, 1150, 870, 835, 770, 725, 705

Working Example 2(1)

Production of 4-(2-bromomethylphenyl)benzonitrile [BMB]

A mixture of 2-(4-methylphenyl)benzonitrile [MPB](271 kg), N-bromosuccinimide [NBS] (256 kg), 2,2'-azobis(2,4-dimethylvaleronitrile) [ABN-V] (543 kg) and methylene chloride (680 kg) was stirred at 45–50° C. under reflux to proceed the reaction, until the percentage of the area of 4-(2-bromomethylphenyl)benzonitrile [BMB] in HPLC becomes 82% or more (for about 2–5 hours). The reaction solution was cooled to 38–42° C. and methylene chloride (250 kg) was added to the solution. To the solution was added water (540 L) and the water layer was separated. The obtained water layer was extracted with methylene chloride 50 kg and the organic layer was collected. This extraction was carried out three times. The methylene chloride layer was concentrated under atmospheric pressure (internal temperature: about 46° C.) to about 700 L (about 2.5 times volume of MPB). To the concentrate was added acetonitrile (about 640 kg) and the solution was concentrated at an internal temperature of 45–55° C. (preferably 45–50° C.) under reduced pressure (about 200–450 mmHg) to about 1100 L. Then, to the concentrate was added acetonitrile (about 480 kg) and the solution was concentrate at an internal temperature of 45–55° C. (preferably 45–50 ° C.) under reduced pressure (about 200–450 mmHg) to about 500 L. To the residue was added acetonitrile (about 480 kg) to give about 1100 L acetonitrile solution containing 2-(4-bromomethylphenyl)benzonitrile [BMB], unreacted 2-(4-methylphenyl)benzonitrile [MPB] and 2-(4,4-dibromomethylphenyl)benzonitrile similar to BMB.

Working Example 2(2)

Production of methyl 2-[N-t-butoxycarbonyl-N-[(2'-cyanobiphenyl-4-yl)-methyl]amino]-3-nitrobenzoate [BBN]

A mixture of methyl 2-t-butoxycarbonylamino-3-nitro benzoate [BAN] (354 kg) obtained in Reference Example 2, acetonitrile solution of 4-(2-bromomethylphenyl) benzonitrile [BMB] obtained in Working Example 2(1) and anhydrous potassium carbonate (475 kg) was added to acetonitrile (1600 kg) and the solution was heated for about 5 hours under reflux (80–85° C.). The reaction solution was cooled and insoluble materials were filtered off and washed with acetonitrile (320 kg). The filtrate and the acetonitrile solution used for washing the insoluble materials were concentrated under reduced pressure to give the concentrate of methyl 2-[N-t-butoxy-carbonyl-N-[(2'-cyanobiphenyl-4-yl)methyl]amino]-3-nitro-benzoate [BBN].

Working Example 2(3)

Production of methyl 2-[[(2'-cyanobiphenyl-4-yl) methyl]amino]-3-nitrobenzoate [MBN]

The concentrate obtained in Working Example 2(2) (methyl2-[N-t-butoxycarbonyl-N-[(2'-cyanobiphenyl-4-yl) methyl]amino]-3-nitro-benzoate [BBN]) and methanol (3200 L) were mixed, and 35% concentrated hydrochloric acid (1050 L) was added to the mixture at 30° C. or less for about 4 hours. The mixture was heated to reflux temperature (67–69° C.) at a speed of 10° C. or less/hour, and stirred for about 1.5 hours under reflux. The reaction solution was cooled, to which was added methanol (800 L), and the solution was stirred at 3–10° C. for about 1 hour. The precipitated crystals were separated, washed with methanol and dried to give methyl 2-[[(2'-cyano-biphenyl-4-yl) methyl]amino]-3-nitro-benzoate [MBN] (407 kg; yield based on MPB: 75%).

m.p. 140–141° C.

$^1$H-NMR (200 MHz, DMSO-d$_6$) δ: 3.84 (3H, s), 4.26 (2H, m), 6.86 (1H, t), 7.46 (2H, d), 7.54–7.65 (4H, m), 7.79 (1H, d), 7.95 (1H, dd), 8.05–8.11 (2H, m), 8.67 (1H, t)

Comparative Example 2(1)

Production and isolation of 2-(4-bromomethylphenyl)benzonitrile [BMB]

A mixture of 2-(4-methylphenyl)benzonitrile [MPB] (30 kg), N-bromosuccinimide [NBS] (28.35 kg), 2,2'-azobis(2, 4-dimethylvalero-nitrile) [ABN-V] (60 g) and methylene chloride (75 kg) was stirred at 45–50° C. for 3–4 hours under reflux and the reaction solution was cooled to 38–42° C. And washed with water (60 kg) three times. The methylene chloride layer was discolored with activated charcoal (0.15 kg) and concentrated under reduced pressure. To the solution was added crystal seeds (0.01 kg), and the solution was cooled to 5° C. or less. The precipitated crystals were separated and dried to give the first crystals of 4-(2-bromomethylphenyl)benzonitrile [BMB] (28.5 kg, 67%). From mother liquor was obtained the second crystals (5.3 kg, 13%).

Comparative Example 2(2)

Production of methyl 2-[N-t-butoxycarbonyl-N-[(2'-cyanobiphenyl-4-yl)-methyl]amino]-3-nitrobenzoate [BBN]

A mixture of methyl 2-t-butoxycarbonylamino-3-nitrobenzoate [BAN] (37.2 kg) obtained in Reference Example 2, 4-(2-bromomethylphenyl)benzonitrile [BMB] (33.8 kg) obtained in Comparative Example 2(1) and anhydrous potassium carbonate (50.3 kg) was added to acetonitrile (312.2 kg) and the solution was heated (80–85° C.) for 5 hours under reflux. The reaction solution was cooled and insoluble materials were isolated. The solution was washed with acetonitrile (38 kg) and the filtrate was concentrated under reduced pressure to obtain the concentrate of methyl 2-[N-t-butoxycarbonyl-N-[(2'-cyanobiphenyl-4-yl)methyl] amino]-3-nitrobenzoate [BBN].

Comparative Example 2(3)

Production of methyl 2-[[(2'-cyanobiphenyl-4-yl) methyl]amino]-3-nitrobenzoate [MBN]

The concentrate (methyl 2-[N-t-butoxycarbonyl-N-[(2'-cyanobiphenyl-4-yl)methyl]amino]-3-nitrobenzoate [BBN])

obtained in Comparative Example 2(2), methanol (190 kg) and 35% concentrated hydrochloric acid (104.0 kg) were mixed and the solution was stirred at 10° C. for 1 hour, and then stirred for 1–1.5 hours under reflux (67° C.). The reaction solution was cooled and methanol (54.3 kg) was added to the solution. The solution was stirred at 3–10° C. for about 1 hour. The precipitated crystals were separated, washed with methanol and dried to give methyl 2-[[(2'-cyanobiphenyl-4-yl)methyl]amino]-3-nitro-benzoate [MBN] (35.6 kg; yield based on MPB: 65%).

m.p. 140–141° C.

$^1$H-NMR (200 MHz, DMSO-d$_6$) δ: 3.84 (3H, s), 4.26 (2H, m), 6.86 (1H, t), 7.46 (2H, d), 7.54–7.65 (4H, m), 7.79 (1H, d), 7.95 (1H, dd), 8.05–8.11 (2H, m), 8.67 (1H, t)

Reference Example 3

Production of methyl 3-amino-2-[[(2'-cyanobiphenyl-4-yl)methyl]amino]benzoate [MBA]

Tin (400 kg) and 35% hydrochloric acid (1322 kg) were mixed, and the solution was stirred at 25–30° C. for about 5 hours. Then, the solution was heated to about 80° C. for about 3 hours and stirred at about 80° C. for about 8 hours to obtain stannous chloride solution.

The MBN solution of methyl 2-[[(2'-cyanobiphenyl-4-yl)methyl]amino]-3-nitrobenzoate [MBN] (400 kg) obtained in Working Example 2(3) and tetrahydrofuran [THF] (1080 kg) was stirred. To the MBN solution was dropped stannous chloride solution at 15–25° C. for 5–8 hours and the reduction was carried out at 15–25° C. for 2–5 hours. After the reaction, the solution was adjusted to pH 12 with 24% sodium hydroxide (about 2000 L) and flake sodium hydroxide (about 177 kg). The organic layer was separated and washed twice with saturated sodium bicarbonate solution (950 L) and thrice with saturated sodium chloride solution (840 L). The organic layer was filtered with 3μ filter and the solution was evaporated. The residue was dissolved in ethyl acetate(540 kg) and the solution was concentrated to obtain the residue containing methyl 3-amino-2-[[(2'-cyanobiphenyl-4-yl)methyl]amino]benzoate [MBA].

Reference Example 4

Production of Tetraethyl Orthocarbonate [TEC]

Under nitrogen atmosphere, NaOEt (530 kg) was dissolved in ethanol (1810 kg) and the solution was heated to about 60° C. To the solution was dropped chloropicrin (264 kg) at 57–64° C. for about 2 hours. The solution was cooled to 35–45° C., and washed with 15.8% sodium chloride solution (8670 kg) and 19.2% sodium chloride solution (1040 kg) in this order. Insoluble materials were centrifuged and the solution was distilled under reduced pressure (88° C., 70 mmHg) to give tetraethyl orthocarbonate [TEC] (180 kg, 58.3%).

Reference Example 5

Production of methyl 1-[(2'-cyanobiphenyl-4-yl) methyl]-2-ethoxy-benzimidazole-7-carboxylate [BEC]

The residue containing methyl 3-amino-2-N-[(2'-cyanobiphenyl-4-yl)methyl] aminobenzoate [MBA] obtained in Reference Example 3, tetraethyl orthocarbonate [TEC] (397 kg) obtained in Reference Example 4 and acetic acid (62 kg) were mixed and the solution was heated for about 1–2 hours under reflux (78–82° C.). The reaction solution was cooled, to which were added methanol (1680 L), 24% sodium hydroxide solution (65 L) and water (2030 L). The solution was stirred at 60–30° C. for 2 hours and adjusted to pH 5–7. The solution was cooled to 5° C. or less and the precipitated crystals were separated and washed with cooled water (2500 L) and cooled ethyl acetate(500 L) to give the first crystals. Mother liquor and solution used for washing the crystals were concentrated under reduced pressure and cooled to 5° C. or less. The precipitated crystals were separated and washed with cooled ethyl acetate (20 L) to give the second crystals. The first and second crystals were dissolved in ethyl acetate (4890 L) under reflux. To the solution were added seed crystals at about 70° C. and the solution was cooled to 5° C. The precipitated crystals were separated, washed with cooled ethyl acetate (200 L) and dried to give methyl 1-[(2'-cyanobiphenyl-4-yl)methyl]-2-ethoxy-benzimidazole-7-carboxylate [BEC] (361 kg, 84.8%).

m.p. 168.5–169.5° C.

$^1$H-NMR (200 MHz, CDCl$_3$) δ: 1.42 (3H, t), 3.71 (3H, s), 4.63 (2H, q), 5.59 (2H, s), 7.09 (2H, d), 7.20 (1H, t), 7.45–7.59 (5H, m), 7.69–7.80 (2H, m), 7.92 (1H, dd)

IR(KBr)cm$^{-1}$: 2225, 1725, 1550, 1480, 1430, 1280, 1250, 1040, 760, 750

Reference Example 6

Production of trioctyltin azide [TOTA]

Sodium azide (160 kg) was dissolved in deionized water (505 L) and the solution was cooled to 3–10° C. To the solution was dropped trioctyltin chloride [TOTC] (847 kg) for 1–3 hours and the solution was stirred at 5–10° C. for about 2 hours. The reaction solution was extracted with methylene chloride (1822 kg, followed by 546 kg). The methylene chloride layer was washed with a mixture of deionized water (50 L) and 10% sodium chloride solution (440 L) and concentrated under reduced pressure to give trioctyltin azide [TOTA].

Reference Example 7

Production of methyl 2-ethoxy-1-[[2'-(1H-tetrazol-5-yl)biphenyl-4-yl]-methyl]benzimidazole-7-carboxylate [MET]

A mixture of methyl 1-[(2'-cyanobiphenyl-4-yl)-methyl]-2-ethoxybenzimidazole-7-carboxylate [BEC] (228 kg) obtained in Reference Example 5, the residue containing trioctyltin azide [TOTA] obtained in Reference Example 6 and toluene (1148 L) was heated for about 40 hours under reflux (115–120° C.). The reaction solution was cooled and concentrated under reduced pressure. To the residue were added ethanol (764 kg) and sodium nitrite solution (135 kg/460 L) and the solution was adjusted to pH 4.5–5.5 with concentrated hydrochloric acid (about 224 kg). To the solution was added ethyl acetate (735 L) and the solution was adjusted to pH 0.5–1.5 with concentrated hydrochloric acid (about 100 L). To the solution was added hexane (1005 L) and the solution was adjusted to pH 3.5±0.5 with 4% sodium hydroxide solution. The solution was cooled to 10° C. or less and stirred for 1 hour. The crystals were separated and washed with a mixture of ethyl acetate (106 L) and hexane (310 L), followed by hexane (410 L) to give wet MET (396.6 kg).

Reference Example 8

Production of 2-ethoxy-1-[[2'-(1H-tetrazol-5-yl) biphenyl-4-yl]methyl]benzimidazole-7-carboxylic acid [Compound A]

To the wet MET(369.6 kg) obtained in Reference Example 9, was added sodium hydroxide solution (73 kg/826 L) and the solution was stirred at 68–72° C. for 1–2 hours. The reaction solution was cooled and washed twice with methylene chloride (486 kg) and once with toluene (366 L). To the aqueous layer was added methanol (1437 L) and the solution was adjusted to pH 7.0±0.5 with concentrated hydrochloric acid (about 35 L). To the solution was added active charcoal (11 kg) and the solution was stirred for about 30 minutes. The active charcoal was filtered off and concentrated hydrochloric acid (about 20 L) was added to the solution until the solution became cloudy. The solution was stirred at 25±5° C. for about 1 hour, to which was added water (487 L), and the solution was adjusted to pH 3.5±0.3 with concentrated hydrochloric acid (about 85 L). The solution was stirred at 24–30° C. for about 30 minutes, to which was added water (687 L), and the solution was cooled to 10° C. or less and stirred for about 1 hour. The crystals were separated, washed with water (412 L) followed by acetone (427 L), crushed and dried to give 2-ethoxy-1-[[2'-(1H-tetrazol-5-yl)biphenyl-4-yl]methyl]benzimidazole-7-carboxylic acid [Compound A] (200 kg, 82.0%).

m.p. 183–185° C.

$^1$H-NMR (200 MHz, DMSO-$d_6$) δ: 1.38 (3H, t), 4.58 (2H, q), 5.63 (2H, s), 6.97 (4H, q), 7.17 (1H, t), 7.47–7.68 (6H, m)

IR(KBr)cm$^{-1}$: 1710, 1550, 1480, 1430, 1280, 1240, 1040, 760

Reference Example 9

Production of 2-ethoxy-1-[[2'-(N-triphenylmethyltetrazol-5-yl)biphenyl-4-yl]methyl]benzimidazole-7-carboxylic acid [Compound A(T)]

In methylene chloride (183 kg) was suspended 2-ethoxy-1-[[2'-(1H-tetrazol-5-yl)biphenyl-4-yl]methyl]benzimidazole-7-carboxylic acid [Compound A] (480 kg) obtained in Reference Example 8. To the suspension was added triethylamine (13.8 kg) to dissolve Compound A. To the solution was added triphenylmethylchloride (34.9 kg) in methylene chloride solution (50 L) and the solution was heated for about 6 hours under reflux (40° C.). To the solution was added methylene chloride (273 kg) and the solution was allowed to stand at room temperature for one night. The reaction solution was heated at 30–35° C., to which was added methanol (81.4 kg). To the solution was added water (205 kg) and the solution was adjusted to pH 3.1±0.2 with 1N hydrochloric acid. The organic layer was separated and concentrated to 288 kg. The concentrate was stirred at room temperature for about 30 minutes, to which was dropped hexane (68 kg) for 20±5 minutes. The resulting mixture was stirred at room temperature for about 30 minutes, followed by at 5±5° C. for about 1 hour. The crystals were separated and washed with a mixture of hexane-methylene chloride (5:1) (205 L). The wet crystals were dissolved in DMF(183 L) and the solution was evaporated to about 138 kg or less to give 2-ethoxy-1-[[2'-(N-triphenylmethyltetrazol-5-yl)biphenyl-4-yl]methyl]benzimidazole-7-carboxylic acid [Compound A(T)] solution (89%).

Reference Example 10

Production of (±)-1-(cyclohexyloxycarbonyloxy) ethyl 2-ethoxy-1-[[2'-(1-triphenylmethyl-1H-tetrazol-5-yl)biphenyl-4-yl]methyl]benzimidazole-7-carboxylate [Compound B(T)]

To the solution of 2-ethoxy-1-[[2'-(N-triphenylmethyltetrazol-5-yl)biphenyl-4-yl]methyl]benzimidazole-7-carboxylic acid [Compound A(T)] obtained in Reference Example 9 were added DMF (68 L), potassium iodide (8.9 kg) and anhydrous potassium carbonate (18.0 kg), and thereafter was added (±)-1-chloroethyl cyclohexylcarbonate [CECC] (23.8 L) at 60° C., and the solution was stirred at 60–70° C. for about 2 hours. The reaction solution was cooled, to which were added water (238 L) and ethyl acetate(402 L). The separated aqueous layer was extracted with ethyl acetate(13 L). The ethyl acetate layers were combined and washed with water (146 L). The ethyl acetate layer was concentrated to 199 kg under reduced pressure. To the residue were added seed crystals and the solution was stirred at room temperature for 2±1 hours to precipitate crystals. To the solution was dropped hexane (267 L) for 20±5 minutes, and stirred at room temperature for 30 minutes, followed by at 5±5° C. for about 1 hour to age the crystals. The crystals were separated, washed twice with a mixture of hexane-ethyl acetate (1:1) (182 L) and dried. The dried crystals were dissolved in methylene chloride (266 kg) to give (±)-1-(cyclohexyloxycarbonyloxy)ethyl 2-ethoxy-1-[[2'-(1triphenylmethyl-1H-tetrazol-5-yl)-biphenyl-4-yl]methyl]-benzimidazole-7-carboxylate [Compound B(T)] solution (95%).

Reference Example 11

Production of (±)-1-(cyclohexyloxycarbonyloxy) ethyl 2-ethoxy-1-[[2'-(1H-tetrazol-5-yl)biphenyl-4-yl]methyl]-1H-benzimidazole-7-carboxylate [Compound B]

To the solution of (±)-1-(cyclohexyloxycarbonyloxy) ethyl 2-ethoxy-1-[[2'-(1-triphenylmethyl-1H-tetrazol-5-yl) biphenyl-4-yl]methyl]benzimidazole-7-carboxylate [Compound B(T)] obtained in Reference Example 10, were added methylene chloride (28 L) and methanol (161 L), and the solution was cooled to −5±5° C. while stirring. To the solution was added dropwise methanolic hydrogen chloride (hydrogen chloride 4.4 kg dissolved in methanol 47 L) at 0° C. or less for 15±5 minutes. The solution was stirred at −5±5° C. for about 2 hours. To the reaction solution were added methylene chloride (209 kg) and pure water (303 L), and the pH of the solution was adjusted to pH about 6.3 at 5° C. or less with 7.0 w/v % sodium bicarbonate solution. The methylene chloride layer was separated, and the aqueous layer was extracted with methylene chloride (209 kg). The methylene chloride layers were combined and washed with water (157 L) and concentrated to 173 kg or less. To the residue was added acetone (124 kg), and the solution was concentrated to 154 kg. To the residue were added ethanol (24 L) and seed crystals, and the solution was stirred at room temperature for 3–5 hours to precipitate crystals. To the resulting mixture was added ethanol (12 L), and the solution was stirred at room temperature for about 30 minutes. To the mixture was added dropwise hexane (363 kg) for about 30 minutes, and the solution was stirred at room temperature for about 1 hour and then at 5±5° C. for about 2 hours to precipitate crystals and age. The separated crystals were separated, washed with a mixture of ethanol-hexane (1:9) (247 L) and dried to give crude crystals of (±)-1-(cyclohexyloxycarbonyloxy)ethyl 2-ethoxy-1-[[2'-(1H-tetrazol-5-yl)biphenyl-4-yl]-methyl]benzimidazole-7-carboxylate [Compound B] (49.5 kg; 88.0%).

Reference Example 12

Production of (±)-1-(cyclohexyloxycarbonyloxy) ethyl 2-ethoxy-1-[[2'-(1H-tetrazol-5-yl)biphenyl-4-yl]methyl]-1H-benzimidazole-7-carboxylate [Compound B] bulk To the crude crystals (about 25 kg) obtained in Reference Example 11 was added acetone (297 kg), and the solution was heated at 45±5° C. to dissolve crystals. To the solution was added active charcoal (0.75 kg), and the solution was stirred for about 30 minutes. The active charcoal was filtered off and washed with acetone (24 kg). The filtrate and the acetone solution used for washing the active charcoal were combined and concentrated under reduced pressure to give 30% w/w solution of Compound B. To the residue was added dropwise warmed (55±2° C.) pure water (8.3 kg), and the solution was stirred for about 10 minutes. To the solution was added dropwise pure water (16.7 kg) for about 5 minutes, and the solution was stirred at 55±2° C. for about 1 hour. The solution was cooled to 25±5° C. for about 30 minutes, and a part of the crystals was picked up to check the crystalline form by the X-ray powder diffraction. To the solution was added a mixture of acetone-pure water (3:1) (about 25 L), and the solution was cooled to 5±5° C. and stirred for about 1 hour. The separated crystals were separated, washed with a mixture of acetone-pure water (3:1) (about 25 L), dried and crushed to give crystals of (±)-1-(cyclohexyloxycarbonyloxy)ethyl 2-ethoxy-1-[[2'-(1H-tetrazol-5-yl)biphenyl-4-yl]methyl]benzimidazole-7-carboxylate [Compound B] (23.0 kg, 93.0%).

What is claimed is:

1. A method for producing a compound of the formula:

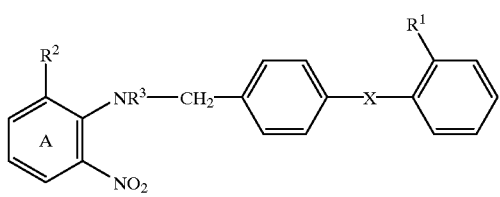

wherein the ring A is a benzene ring which may have an optional substituent selected from (1) halogen, (2) cyano, (3) a nitro group, (4) an optionally substituted lower ($C_{1-4}$) alkyl, (5) a lower ($C_{1-4}$) alkoxy, (6) an optionally substituted amino group, (7) a group of the formula: —CO—D' wherein D' is hydroxy group or an optionally substituted lower ($C_{1-4}$) alkoxy whose alkyl moiety may be substituted with hydroxy group, a lower ($C_{1-4}$) alkoxy, a lower ($C_{2-6}$) alkanoyloxy, a lower ($C_{1-6}$) alkoxy-carbonyloxy, a lower ($C_{3-6}$) cycloalkoxycarbonyloxy or (8) tetrazolyl, trifluoromethanesulfonamido group, phosphono group, sulfo group, each of which may be protected by an optionally substituted lower ($C_{1-4}$) alkyl or acyl; in addition to the group $R^2$, the nitro group and the group of the formula:

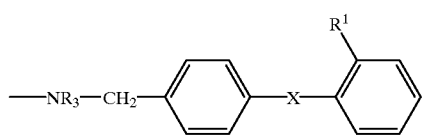

$R^1$ is a group capable of forming an anion or transformable thereinto;
$R^2$ is a group capable of forming an anion or transformable thereinto;
$R^3$ is an acyl group; and
X is a direct bond, a lower ($C_{1-4}$) alkylene in which the number of atoms composing the straight chain is 1 or 2, —CO—, —O—, —S—, —NH—, —CO—NH—, —O—$CH_2$—, —S—$CH_2$— or —CH=CH—; or a salt thereof, said method comprises reacting a mixture containing (i) a mono-halogeno compound of the formula:

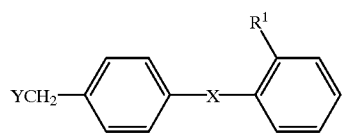

wherein Y is a halogen atom and the other symbols are as defined above, or a salt thereof and (ii) a di-halogeno compound of the formula:

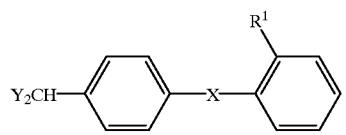

wherein each symbol is as defined above, or a salt therof, wherein, in said mixture, the di-halogeno compound is present in an amount of about 1/20 to 1 mole per mol of the mono-halogeno compound, with a compound of the formula:

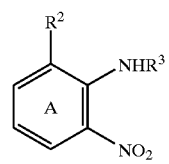

wherein the ring A is a benzene ring which may have an optional substituent as defined above in addition to the group $R^2$, the nitro group and the group of formula: —$NHR^3$ and the other symbols are defined above, or a salt thereof.

2. A method according to claim 1, wherein said reaction is carried out in acetonitrile.

3. A method according to claim 1, wherein Y is a bromine atom.

4. A method according to claim 1, wherein $R^1$ is (1) a carboxyl group, (2) a tetrazolyl group, (3) a trifluoromethanesulfonamido group, (4) a phosphono group, (5) a sulfo group, or (6) a 5–7 membered monocyclic heterocyclic group which contains one or more of N, S and O and which may be substituted.

5. A method according to claim 4, wherein the heterocyclic group is a group of the formula:

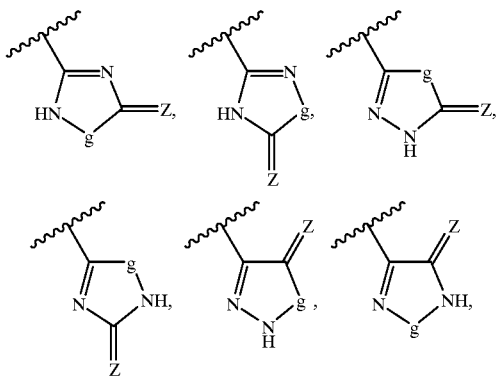

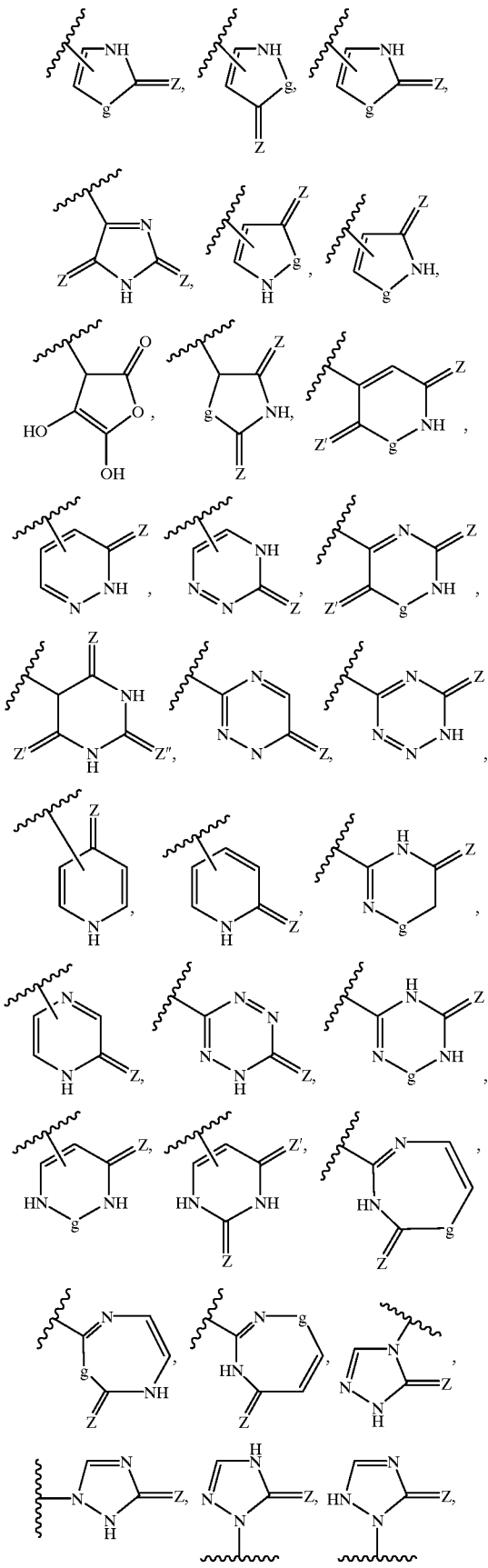

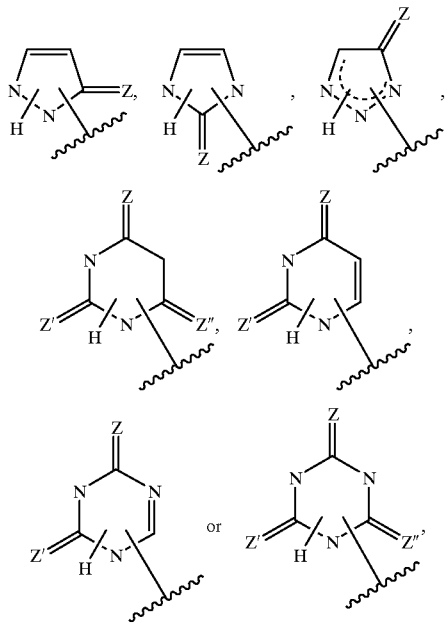

wherein g is —CH$_2$—, —NH—, —O— or —S(O)m—; >=Z, >=Z' and >=Z" are each individually selected from a carbonyl group, a thiocarbonyl group or an optionally oxidized sulfur atom; and m is an integer of 0, 1 or 2, said heterocyclic group may be protected by an optionally substituted lower (C$_{1-4}$) alkyl group or an acyl group and said heterocyclic group may be substituted with an optionally substituted lower (C$_{1-4}$) alkyl group, a halogen atom, a nitro group, cyano, a lower (C$_{1-4}$)alkoxy group or an amino group optionally substituted with 1–2 lower (C$_{1-4}$) alkyl groups.

6. A method according to claim 4, wherein the heterocyclic group is an oxadiazolone ring, an oxadiazolothione ring or a thiadiazolone ring, which may be protected by an optionally substituted lower (C$_{1-4}$) alkyl group or an acyl group.

7. A method according to claim 4, wherein the heterocyclic group is a tetrazolyl group or a group of the formula:

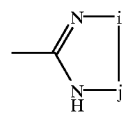

wherein the symbol i is —O— or —S—, the symbol j is >C=O, >C=S or >S(O)m, and m is an integer of 0, 1 or 2.

8. A method according to claim 1, wherein R$^1$ is (1) carboxyl, tetrazolyl or 2,5-dihydro-5-oxo-1,2,4-oxadiazol-3-yl each of which may be protected with an optionally substituted lower (C$_{1-4}$) alkyl or acyl group, or (2) cyano or N-hydroxycarbamimidoyl.

9. A method according to claim 1, wherein R$^1$ is cyano.

10. A method according to claim 1, wherein X is a direct bond.

11. A method according to claim 1, wherein the ring A has no substituent in addition to the group R$^2$, the nitro group and the group of the formula: —NHR$^3$ unsubstituted or substituted with a group of the formula:

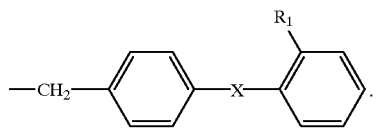

12. A method according to claim 1, wherein $R^2$ is (1) an optionally esterified or amidated carboxyl group, (2) tetrazolyl group, (3) trifluoromethanesulfonamido group, (4) phosphono group or (5) sulfo group, each may be protected by an optionally substituted lower alkyl group or an acyl group.

13. A method according to claim 1, wherein $R^2$ is a group of the formula: —CO—D wherein D is an optionally substituted alkoxy group.

14. A method according to claim 1, wherein $R^2$ is a group of the formula: —CO—D wherein D is (1) hydroxy group or (2) a lower ($C_{1-4}$) alkoxy whose alkyl moiety may be substituted with hydroxy, amino, halogen, lower ($C_{2-6}$) alkanoyloxy, lower ($C_{3-8}$) cycloalkanoyloxy, lower ($C_{1-6}$) alkoxycarbonyloxy, lower ($C_{3-8}$) cycloalkoxycarbonyloxy, lower ($C_{1-4}$) alkoxy or lower ($C_{3-8}$) cycloalkoxy.

15. A method according to claim 1, wherein $R^2$ is a methoxycarbonyl group.

16. A method according to claim 1, wherein $R^3$ is a group of the formula: —$COR^8$ or —$COOR^8$ wherein $R^8$ is an optionally substituted hydrocarbon residue.

17. A method according to claim 16, wherein $R^8$ is a lower ($C_{1-5}$) alkyl or a lower ($C_{2-5}$) alkenyl group optionally substituted with hydroxy group, amino group, halogen or a lower ($C_{1-4}$) alkoxy group.

18. A method according to claim 1, wherein $R^3$ is t-butoxycarbonyl.

19. A method according to claim 1, wherein said reaction is carried out in the presence of potassium carbonate in acetonitrile.

20. A method according to claim 1, wherein said reaction is carried out between (1) a mixture containing 2-(4-bromomethylphenyl)benzonitrile and 2-(4,4-dibromomethylphenyl)benzonitrile and (2) methyl 2-tert-butoxycarbonylamino-3-nitrobenzoate to give methyl 2-[N-t-butoxycarbonyl-N-[(2'-cyano-biphenyl-4-yl)methyl]amino]-3-nitrobenzoate.

21. A method for producing a compound of formula:

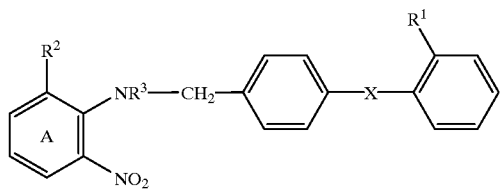

wherein the ring A is a benzene ring which may have an optional substituent selected from (1) halogen, (2) cyano, (3) a nitro group, (4) an optionally substituted lower ($C_{1-4}$) alkyl, (5) a lower ($C_{1-4}$) alkoxy, (6) an optionally substituted amino group, (7) a group of the formula: —CO—D' wherein D' is hydroxy group or an optionally substituted lower ($C_{1-4}$) alkoxy whose alkyl moiety may be substituted with hydroxy group, a lower ($C_{1-4}$) alkoxy, a lower ($C_{2-6}$) alkanoyloxy, a lower ($C_{1-6}$) alkoxy-carbonyloxy, a lower ($C_{3-6}$) cycloalkoxycarbonyloxy or (8) tetrazolyl, trifluoromethanesulfonamido group, phosphono group, sulfo group, each of which may be protected by an optionally substituted lower ($C_{1-4}$) alkyl or acyl; in addition to the group $R^2$, the nitro group and the group of the formula:

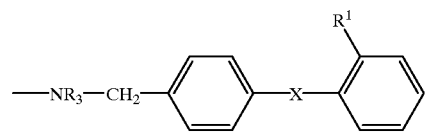

$R^1$ is a group capable of forming an anion or transformable thereinto;
$R^2$ is a group capable of forming an anion or transformable thereinto;
$R^3$ is an acyl group; and
X is a direct bond, a lower ($C_{1-4}$) alkylene in which the number of atoms composing the straight chain is 1 or 2, —CO—, —O—, —S—, —NH—, —CO—NH—, —O—$CH_2$—, —S—$CH_2$— or —CH=CH—; or a salt thereof,
said method comprises
preparing a reaction mixture by subjecting a compound of the formula:

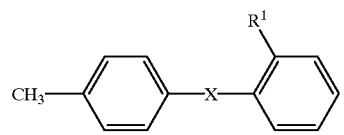

wherein $R^1$ and X is defined above or a salt thereof to halogenation to form a mixture containing
(i) a mono-halogeno compound of the formula:

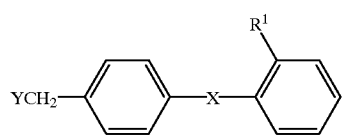

wherein Y is a halogen atom and the other symbols are as defined above, or a salt thereof and
(ii) a di-halogeno compound of the formula:

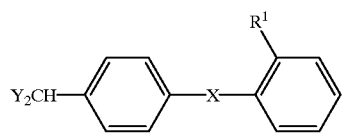

wherein each symbol is as defined above, or a salt thereof, wherein, in said mixture, the di-halogeno compound is present in an amount of about 1/20 to 1 mole per mol of the mono-halogeno compound; and
reacting said mixture with a compound of the formula:

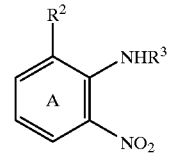

wherein the ring A is a benzene ring which may have an optional substituent as defined above in addition to the group $R^2$, the nitro group and the group of the formula: —$NHR^3$ and the other symbols are defined above, or a salt thereof.

* * * * *